US007019153B2

(12) United States Patent
Borase et al.

(10) Patent No.: US 7,019,153 B2
(45) Date of Patent: Mar. 28, 2006

(54) PROCESS FOR HYDROGENOLYSIS OF [1-(3-DIMETHYLAMINO)PROPYL)]-1-(4-FLUOROPHENYL)-1,3-DIHYDRO-5-HALO-ISOBENZOFURAN ACETAMIDO-3-SUBSTITUTED-3-CEPHEM-4-CARBOXYLIC ACID

(75) Inventors: Ashok Punju Borase, Baroda (IN); Nileshkumar Sureshbhai Patel, Baroda (IN); Srinivasu Kilaru, Baroda (IN); Rajamannar Thennati, Baroda (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 62 days.

(21) Appl. No.: 10/865,139

(22) Filed: Jun. 8, 2004

(65) Prior Publication Data

US 2005/0004380 A1 Jan. 6, 2005

(30) Foreign Application Priority Data

Jun. 10, 2003 (IN) ........................ 602/MUM/2003

(51) Int. Cl.
*C07D 307/87* (2006.01)

(52) U.S. Cl. ...................................................... 549/467

(58) Field of Classification Search ................. 549/467
See application file for complete search history.

(56) References Cited

U.S. PATENT DOCUMENTS

| | | | |
|---|---|---|---|
| 4,136,193 | A | 1/1979 | Bogeso et al. |
| RE34,712 | E | 8/1994 | Boegesoe et al. |
| 6,455,710 | B1 | 9/2002 | Villa et al. |
| 2001/0031784 | A1 | 10/2001 | Petersen et al. |
| 2002/0077353 | A1 | 6/2002 | Petersen et al. |
| 2003/0078442 | A1 | 4/2003 | Petersen et al. |

FOREIGN PATENT DOCUMENTS

| | | |
|---|---|---|
| WO | 98/19512 | 5/1998 |
| WO | 98/19513 | 5/1998 |
| WO | 99/30548 | 6/1999 |
| WO | 00/11926 | 3/2000 |
| WO | 00/23431 | 4/2000 |
| WO | 01/47877 | 7/2001 |
| WO | 03/029236 | 4/2003 |

*Primary Examiner*—Bernard Dentz
(74) *Attorney, Agent, or Firm*—Merchant & Gould P.C.

(57) ABSTRACT

The present invention provides a process for decreasing the content of [1-(3-dimethylamino)propyl)]-1-(4-fluorophenyl)-1,3-dihydro-5-halo-isobenzofuran, a compound of formula 1, wherein X is halogen, Formula 1

X CH$_3$ N CH$_3$ O F by converting to a compound of formula 3,

Formula 3

O CH$_3$ N CH$_3$ F comprising subjecting [1-(3-dimethylamino)propyl)]-1-(4-fluorophenyl)-1,3-dihydro-5-halo-isobenzofuran present as impurity in crude 1-[3-(dimethylamino)propyl]-1-(4-fluorophenyl)-1,3-dihydro-5-isobenzofuran carbonitrile to hydrogenolysis.

23 Claims, No Drawings

PROCESS FOR HYDROGENOLYSIS OF [1-(3-DIMETHYLAMINO)PROPYL)]-1-(4-FLUOROPHENYL)-1,3-DIHYDRO-5-HALO-ISOBENZOFURAN ACETAMIDO-3-SUBSTITUTED-3-CEPHEM-4-CARBOXYLIC ACID

The present invention relates to a process for decreasing the content of [1-(3-dimethylamino)propyl)]-1-(4-fluorophenyl)-1,3-dihydro-5-halo-isobenzofuran, a compound of formula 1, wherein X is halogen, Formula 1

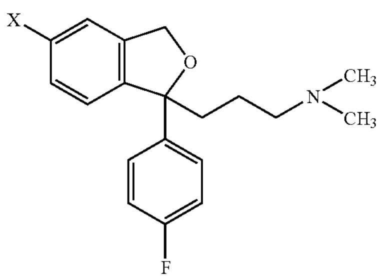

by converting to a compound of formula 3, comprising

Formula 3

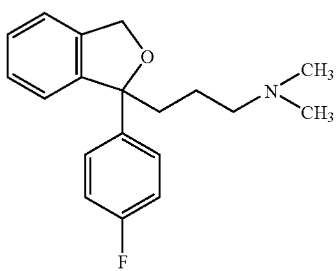

subjecting [1-(3-dimethylamino)propyl)]-1-(4-fluorophenyl)-1,3-dihydro-5-halo-isobenzofuran present as impurity in crude 1-[3-(dimethylamino)propyl]-1-(4-fluorophenyl)-1,3-dihydro-5-isobenzofuran carbonitrile to hydrogenolysis.

The present invention also relates to a process for purification of 1-[3-(dimethylamino)propyl]-1-(4-fluorophenyl)-1,3-dihydro-5-isobenzofuran carbonitrile comprising, a) subjecting crude 1-[3-(dimethylamino)propyl]-1-(4-fluorophenyl)-1,3-dihydro-5-isobenzofuran carbonitrile having impurity of [1-(3-dimethylamino)propyl)]-1-(4-fluorophenyl)-1,3-dihydro-5-halo-isobenzofuran, a compound of formula 1, Formula 1

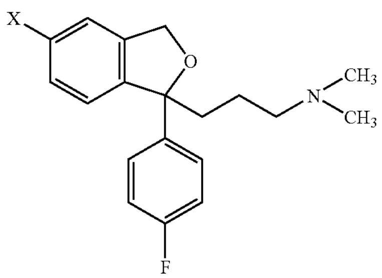

wherein X is halogen, to hydrogenolysis, b) optionally converting the resulting crude 1-[3-(dimethylamino)propyl]-1-(4-fluorophenyl)-1,3-dihydro-5-isobenzofuran carbonitrile to an acid addition salt thereof, and c) purifying and isolating the resulting 1-[3-(dimethylamino)propyl]-1-(4-fluorophenyl)-1,3-dihydro-5-isobenzofuran carbonitrile as a base or a pharmaceutically acceptable salt thereof.

1-[3-(Dimethylamino)propyl]-1-(4-fluorophenyl)-1,3-dihydro-5-isobenzofuran carbonitrile, a compound of formula 2, commonly known as citalopram (INN name), is a well known antidepressant.

Formula 2

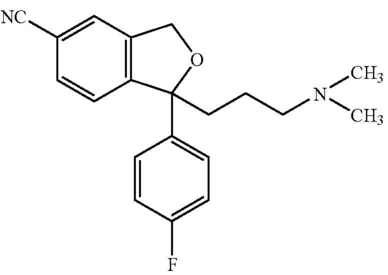

The preparation of 1-[3-(dimethylamino)propyl]-1-(4-fluorophenyl)-1,3-dihydro-5-isobenzofuran carbonitrile was first disclosed in U.S. Pat. No. 4,136,193 (Indian reference not available). Subsequently several other patents appeared in the literature regarding enriching crude citalopram base or salt purity so as to obtain pharmaceutically acceptable base or acid addition salts.

U.S. Pat. No. 4,136,193 (hereinafter referred to as the '193 patent) claims 1-[3-(dimethylamino) propyl]-1-(4-fluorophenyl)-1,3-dihydro-5-isobenzofuran carbonitrile and its pharmaceutically acceptable acid addition salts. It discloses a process for the preparation of 1-[3-(dimethylamino) propyl]-1-(4-fluorophenyl)-1,3-dihydro-5-isobenzofuran carbonitrile from the compound of formula 1

Formula 1

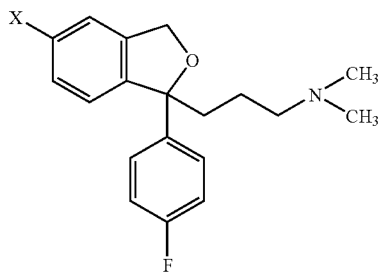

wherein X is halogen or triflates, by reaction with a cyanide source. In this process wherein the group 'X' is replaced with the cyano group is referred to as cyanide exchange process hereinafter.

The cyanide exchange process as illustrated in example 2 of the '193 patent provides citalopram crude base as an oil. It contains unreacted starting compound and many other impurities such as the halo impurity, a compound of formula 1; the descyano impurity, a compound of formula 3; the amide impurity, a compound of formula 4; the desmethyl impurity, a compound of formula 5; the desfluro impurity, a compound of formula 6; the 3-oxo impurity, a compound of formula 7 and the N-oxide impurity, a compound of formula 8.

Formula 3

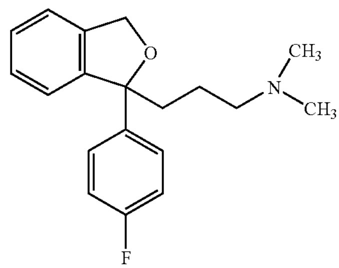

Formula 4

Formula 5

-continued

Formula 6

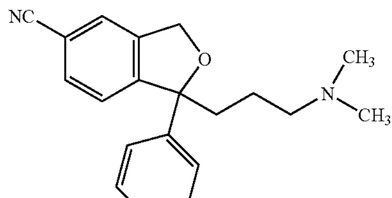

Formula 7

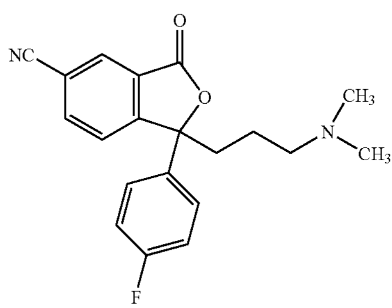

Formula 8

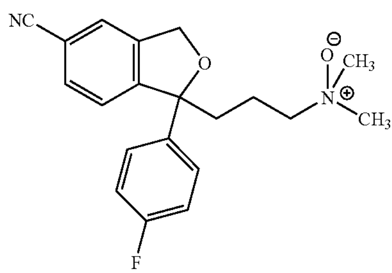

Several other patents for newer synthetic methods have also been reported in the literature for preparing citalopram relating to conversion of 5-substituent of isobenzofuran ring to 5-cyano group, as mentioned below:

1. Conversion 5-amido or ester group to a 5-cyano group: (WO 9819513)
2. Conversion 5-amino group to a 5-Cyano group (WO 9819512)
3. Conversion 5-formyl group to a 5-Cyano group (WO 9930548)
4. Conversion 5-oxazolinyl or thiazolinyl group to a 5-Cyano group (WO 0023431)
5. Conversion 5-halo group to a 5-Cyano group (WO 0011926)
6. Conversion 5-halo group to a 5-Cyano group (WO 0013648)

The international application WO 0147877 discloses preparation of 1-[3-(dimethylamino) propyl]-1-(4-fluorophenyl)-1,3-dihydro-5-isobenzofuran carbonitrile, by the cyanide exchange process in sulfolane solvent, instead of dimethylformamide solvent as in example 2 of the '193 patent. It is reported that the cyanide exchange process for preparation of citalopram as in the '193 patent, gives some high molecular weight impurities including dimeric reaction products in unacceptable amounts and that these impurities are difficult to remove by usual working up procedures leading to extensive and expensive purification processes. Even using sulfolane as a solvent the purity reported by HPLC is about 85%, which is further purified by film distillation process to obtain citalopram of 96% purity.

The international application WO 0145483 (the U.S. Pat. No. 6,455,710 is its equivalent) discloses a cyanide exchange process for preparation of 1-[3-(dimethylamino) propyl]-1-(4-fluorophenyl)-1,3-dihydro-5-isobenzofuran carbonitrile from the compounds of formula 1, wherein the group X is selected from chloro, bromo, iodo or $CF_3$—$(CF_2)_n$—$SO_2$—O—, n being from 0 to 8, by reaction with a cyanide source and subsequently treating the resultant crude citalopram with an amide or an amide-like group forming agent for removing desmethyl impurity, a compound of formula 5,

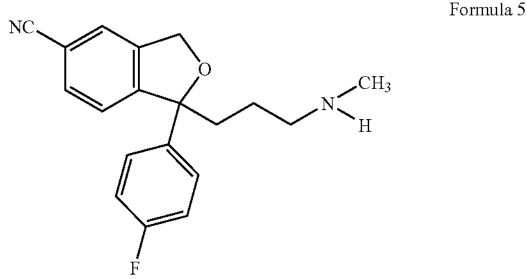

Formula 5 generated during cyanide exchange process. This PCT application teaches that desmethyl impurity is removed by reacting with a reagent that converts it into amide or an amide-like neutral derivative, which subsequently can be removed by subjecting to an acid/base treatment and/or crystallization and recrystallization of citalopram. The reagents like acid halides, acid anhydrides have been disclosed for removal of desmethyl impurity. Acetic anhydride and acetyl chloride are the preferred reagents and use of acetic anhydride has been exemplified. However, this method does not remove the unreacted starting compound of formula 1.

The end product obtained by the above-mentioned prior art processes is crude citalopram in an oil form which contains impurity of the unreacted starting compound of formula 1, which is difficult to remove.

In general the processes described generates many of the side products, which needs to be removed in order to make pharmaceutically acceptable citalopram product. The international application WO 0013648 (equivalent of United States patent application US 2002/0077353 A1) states that in the cyanide exchange process, the exchange of 5-bromo group (compound of formula 1, X is bromo) to 5-cyano is not very convenient in commercial scale, since the yield was rather low, the product was impure and in particular that it was very difficult to separate the resulting citalopram from the corresponding starting 5-bromo compound.

The reissued U.S. Pat. RE No. 34712 describes synthesis of crystalline citalopram base in example 3, starting from a racemic diol via a methanesulfonyl ester in dichloromethane in presence of triethylamine. The reaction mixture was washed with 0.1M NaOH solution and the organic phase evaporated to obtain a crystalline citalopram base.

International application WO 0168627 (equivalent United States patent applications US 2001/0031784 A1 and US 2003/0078442) describes a process for purification of citalopram base to obtain 99.8% w/w pure, preferably more than 99.9% w/w pure crystalline base. As can be seen from example 1 of WO 01/68627, the citalopram hydrobromide is suspended in water and toluene, neutralized by addition of NaOH, the organic phase is washed with water and concentrated in vacuum and the obtained citalopram base that is still in an oil form is crystallized from n-heptane.

The international application WO 03/029236 discloses a process for removal of desmethyl impurity, a compound of formula 5, and its demethylated derivative by contacting crude citalopram with a scavenger resin having a reactive amine functional group, wherein the impurities become resin bound.

The major impurity that is extremely difficult to remove from 1-[3-(dimethylamino)propyl]-1-(4-fluorophenyl)-1,3-dihydro-5-isobenzofuran carbonitrile when it is prepared by a cyanide exchange process is the starting compound represented by a compound of formula 1, wherein X is halogen. The present invention provides a

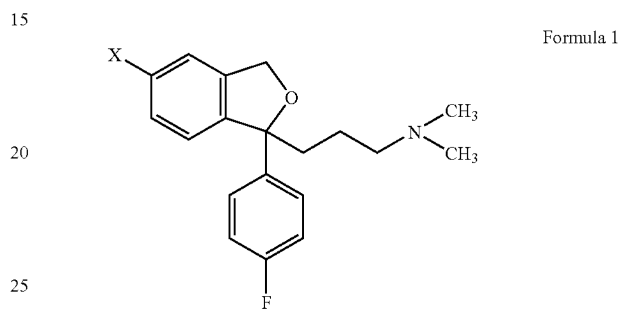

Formula 1 process for decreasing the content of the compound of formula 1 present as impurity in 1-[3-(dimethylamino)propyl]-1-(4-fluorophenyl)-1,3-dihydro-5-isobenzofuran carbonitrile by subjecting to hydrogenolysis.

OBJECTIVES OF THE INVENTION

The objective of the present invention is to provide a process for decreasing the content of [1-(3-dimethylamino) propyl)]-1-(4-fluorophenyl)-1,3-dihydro-5-halo-isobenzofuran, a compound of formula 1,

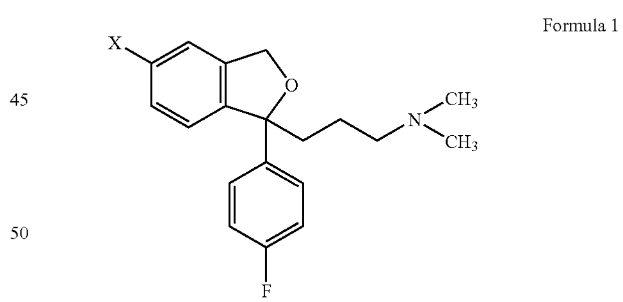

Formula 1 wherein X is halogen, present as impurity in 1-[3-(dimethylamino)propyl]-1-(4-fluorophenyl)-1,3-dihydro-5-isobenzofuran carbonitrile by subjecting to hydrogenolysis.

Another objective of the present invention is to provide a process for purification of 1-[3-(dimethylamino)propyl]-1-(4-fluorophenyl)-1,3-dihydro-5-isobenzofuran carbonitrile, a compound of formula 2 by converting the impurity of compound of formula 1 present in the compound of formula 2, to a compound of formula 3, by subjecting the crude compound of formula 2 to hydrogenolysis, wherein the compound of formula 3 can be relatively easily removed by conventional purification steps.

SUMMARY OF THE PRESENT INVENTION

The present invention provides a process for decreasing the content of [1-(3-dimethylamino)propyl)]-1-(4-fluorophenyl)-1,3-dihydro-5-halo-isobenzofuran, a compound of formula 1, wherein X is halogen,

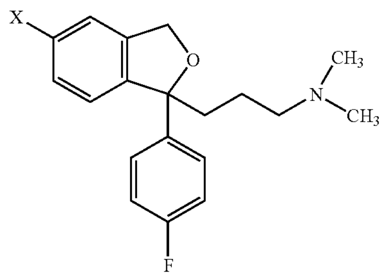
Formula 1 by converting to a compound of formula 3, comprising

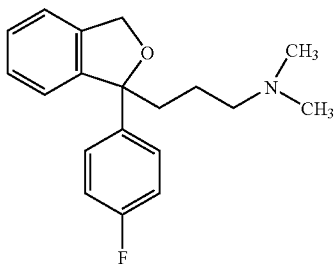
Formula 3 subjecting [1-(3-dimethylamino)propyl)]-1-(4-fluorophenyl)-1,3-dihydro-5-halo-isobenzofuran present as impurity in crude 1-[3-(dimethylamino)propyl]-1-(4-fluorophenyl)-1,3-dihydro-5-isobenzofuran carbonitrile to hydrogenolysis.

In another aspect the present invention provides a process for purification of 1-[3-(dimethylamino)propyl]-1-(4-fluorophenyl)-1,3-dihydro-5-isobenzofuran carbonitrile comprising, a) subjecting crude 1-[3-(dimethylamino)propyl]-1-(4-fluorophenyl)-1,3-dihydro-5-isobenzofuran carbonitrile having impurity of [1-(3-dimethylamino)propyl)]-1-(4-fluorophenyl)-1,3-dihydro-5-halo-isobenzofuran, a compound of formula 1,

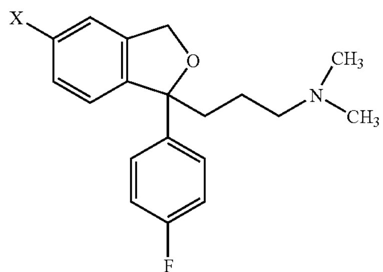
Formula 1 wherein X is halogen, to hydrogenolysis, b) optionally converting the resulting crude 1-[3-(dimethylamino)propyl]-1-(4-fluorophenyl)-1,3-dihydro-5-isobenzofuran carbonitrile to an acid addition salt thereof, and c) purifying and isolating the resulting 1-[3-(dimethylamino)propyl]-1-(4-fluorophenyl)-1,3-dihydro-5-isobenzofuran carbonitrile as a base or a pharmaceutically acceptable salt thereof.

DETAILED DESCRIPTION OF THE INVENTION

The present invention provides a process for hydrogenolysis of [1-(3-dimethylamino)propyl)]-1-(4-fluorophenyl)-1,3-dihydro-5-halo-isobenzofuran, a compound of formula 1,

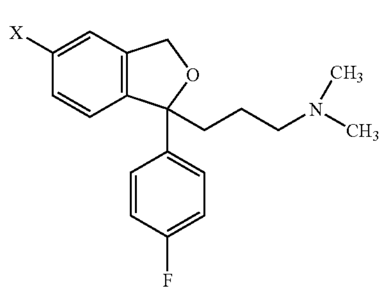
Formula 1 wherein X is halogen, present as impurity in crude 1-[3-(dimethylamino)propyl]-1-(4-fluorophenyl)-1,3-dihydro-5-isobenzofuran carbonitrile. The hydrogenolysis is carried out in presence of a catalyst and a hydrogen source.

Crude 1-[3-(dimethylamino)propyl]-1-(4-fluorophenyl)-1,3-dihydro-5-isobenzofuran carbonitrile as referred to herein refers to 1-[3-(dimethylamino)propyl]-1-(4-fluorophenyl)-1,3-dihydro-5-isobenzofuran carbonitrile having more than 0.1% of [1-(3-dimethylamino)propyl)]-1-(4-fluorophenyl)-1,3-dihydro-5-halo-isobenzofuran, a compound of formula 1.

Hydrogenolysis as referred to herein has the generally accepted meaning in the art, for example, it may be described as a reaction involving the cleavage of a chemical bond in an organic compound with subsequent addition of a hydrogen atom.

The catalyst may be selected from precious metals for example, palladium, platinum, rhodium and the like on active carbon or nickel and various forms of nickel for example, raney nickel, preferably palladium on carbon (Pd/C) or raney nickel, more preferably palladium on carbon.

The hydrogen source may be for example, hydrogen gas, ammonium formate, sodium hypophosphite and the like. Preferred hydrogen source is selected from ammonium formate and sodium hypophosphite.

In the process of the present invention the hydrogenolysis reaction may be carried out in an aqueous or non-aqueous solvent. Examples of solvents that may be used include ethylacetate, dichloromethane, an alcohol, water or mixture thereof. The preferred solvent is ethylacetate.

In the process of the present invention the hydrogenolysis reaction is carried out at temperature between the range of 0° C. to 150° C., preferably between the range of 15° C. to 100° C. and more preferably between the range of 25° C. to 80° C.

In the process of the present invention if hydrogen is used as the hydrogen source then the hydrogen pressure is maintained between 0 to 100 psi, preferably 0 to 30 psi, more preferably at atmospheric pressure.

In the process of the present invention the hydrogenolysis reaction is carried out for a period of about 30 minutes to about 24 hours, preferably about 1 to about 15 hours, more preferably about 2 to about 7 hours.

In one preferred embodiment of the present invention the catalyst is palladium on carbon and the hydrogen source is ammonium formate and the hydrogenolysis reaction is carried out in ethyl acetate solvent at reflux temperature for a period of about 2 to about 7 hours.

In another preferred embodiment of the present invention, the catalyst is palladium on carbon and the hydrogen source is sodium hypophosphite and the hydrogenolysis reaction is carried out in ethyl acetate solvent at reflux temperature for a period of about 2 to about 7 hours.

In yet another preferred embodiment of the present invention, the catalyst is palladium on carbon and the hydrogen source is hydrogen and the hydrogenolysis reaction is carried out at hydrogen pressure between the range of 0 to 100 psi.

In still another preferred embodiment of the present invention the catalyst is palladium on carbon and the hydrogen source is hydrogen and the hydrogenolysis reaction is carried out at atmospheric pressure.

Further the present invention provides a process for purification of 1-[3-(dimethylamino)propyl]-1-(4-fluorophenyl)-1,3-dihydro-5-isobenzofuran carbonitrile comprising, a) subjecting crude 1-[3-(dimethylamino)propyl]-1-(4-fluorophenyl)-1,3-dihydro-5-isobenzofuran carbonitrile having impurity of [1-(3-dimethylamino)propyl)]-1-(4-fluorophenyl)-1,3-dihydro-5-halo-isobenzofuran, a compound of formula 1, Formula 1

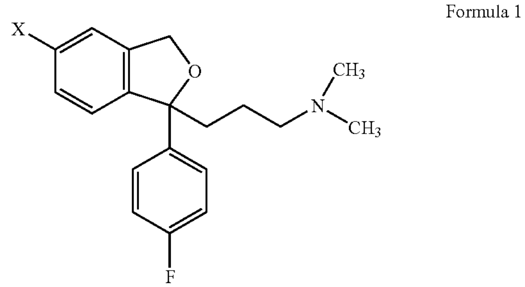

wherein X is halogen, to hydrogenolysis, b) optionally converting the resulting crude 1-[3-(dimethylamino)propyl]-1-(4-fluorophenyl)-1,3-dihydro-5-isobenzofuran carbonitrile to an acid addition salt thereof, and c) purifying and isolating the resulting 1-[3-(dimethylamino)propyl]-1-(4-fluorophenyl)-1,3-dihydro-5-isobenzofuran carbonitrile as a base or a pharmaceutically acceptable salt thereof.

The purification of the crude compound of formula 2 resulting after hydrogenolysis, can be carried out by employing usual work up procedures known in the art. For example, the crude compound of formula 2 obtained after hydrogenolysis process of the present invention can be converted to an acid addition salt thereof, for example oxalate, hydrochloride, hydrobromide, sulphate and the like, which can be purified by recrystallization from a suitable organic solvent, repeatedly if desired to obtain the pharmaceutically acceptable salt of 1-[3-(dimethylamino)propyl]-1-(4-fluorophenyl)-1,3-dihydro-5-isobenzofuran carbonitrile, a compound of formula 2.

The process of the present invention particularly relates to the removal of halo impurities, compound of formula 1, which may be present up to the extent of 10% by wt of the 1-[3-(dimethylamino)propyl]-1-(4-fluorophenyl)-1,3-dihydro-5-isobenzofuran carbonitrile, by subjecting the crude 1-[3-(dimethylamino)propyl]-1-(4-fluorophenyl)- 1,3-dihydro-5-isobenzofuran carbonitrile to a simple mild hydrogenolysis reaction, wherein the halo impurities represented by a compound of formula 1 are converted to the compound of formula 3, which can be easily removed in the work up procedures.

Thus the present invention provides a novel process for purification of compound of formula 2 containing the halo impurities represented by compound of formula 1 by subjecting crude compound of formula 2 to hydrogenolysis, wherein the compound of formula 1 is converted to a compound of formula 3. The compound of formula 3 can be easily removed in the usual work up procedures such that pharmaceutically acceptable compound of formula 2 is obtained. The other related impurities like descyano, desfluoro, 3-oxo, amide, N-oxide and desmethyl impuirties also get removed during the work up process. In particular, the presence of halo impurities of formula 1, which are found to be difficult to remove makes 1-[3-(dimethylamino)propyl]-1-(4-fluorophenyl)-1,3-dihydro-5-isobenzofuran carbonitrile product pharmaceutically not acceptable and the present invention provides a convenient process for removal of halo impuritiy of formula 1 by converting it to compound of formula 3, when the crude 1-[3-(dimethylamino)propyl]-1-(4-fluorophenyl)-1,3-dihydro-5-isobenzofuran carbonitrile containing the halo impurity of formula 1 is subjected to hydrogenolysis.

In the process of the present invention the halo impurities represented by compound of formula 1 present as impurity in compound of formula 2, get converted to compound of formula 3, when compound of formula 2 is subjected to hydrogenolysis. The advantage lies in the fact that unlike halo impurities represented by compound of formula 1, it is easier to remove the compound of formula 3 from the compound of formula 2 by following routine work up procedures, for example by forming acid addition salt of compound of formula 2 and its purification by recrystallizastion from a suitable organic solvent.

Any acid addition salt of compound of formula 2 can be prepared, for example oxalate, hydrobromide, hydrochloride, sulfate salt and the like, preferably an oxalate salt of compound of formula 2. The oxalate salt of compound of formula 2 is prepared/purified using a suitable solvent, preferably acetone, ethyl acetate or isopropanol, more preferably selected from acetone or ethyl acetate.

In a preferred embodiment the acid addition salt is the oxalate salt of compound of formula 2 and it is prepared and if desired purified by recrystallization from acetone.

The acid addition salt of compound of formula 2, for example the oxalate salt can be converted to a pharmaceutically acceptable salt of compound of formula 2, for example the hydrobromide salt. If desired the hydrobromide salt of compound of formula 2 can be purified by recrystallization from a suitable solvent, repeatedly if desired till pharmaceutically acceptable salt of compound of formula 2 is obtained. Examples of solvents include acetone, methanol, ethyl acetate, dimethyl formamide, isopropanol or mixtures thereof. The preferred solvents for purification of hydrobromide salt of compound of formula 2 are solvent system of methanol and ethyl acetete, or dimethyl formamide and isopropanol.

In another preferred embodiment the oxalate salt of compound of formula 2 is prepared, optionally purified by recrystallization from acetone, then neutralized by treatment with a convenient base for example NaOH or ammonia, to generate free base of compound of formula 2. The free base of compound of formula 2 is converted to pharmaceutically acceptable salt thereof such as hydrobromide salt of compound of formula 2, the hydrobromide salt of compound of formula 2 is then recrystallized from solvent system of methanol and ethyl acetate.

In one preferred embodiment the process of the present invention provides a pharmaceutically acceptable salt of 1-[3-(dimethylamino)propyl]-1-(4-fluorophenyl)-1,3-dihydro-5-isobenzofuran carbonitrile having purity greater than 99.5%.

In another preferred embodiment the process of the present invention provides a pharmaceutically acceptable salt of 1-[3-(dimethylamino)propyl]-1-(4-fluorophenyl)-1,3-dihydro-5-isobenzofuran carbonitrile having purity greater than 99.8%.

The process of the present invention provides a process for recrystallization of the hydrobromide salt of 1-[3-(dimethylamino)propyl]-1-(4-fluorophenyl)-1,3-dihydro-5-isobenzofuran carbonitrile comprising dissolving in a solvent system of dimethyl formamide:isopropanol, cooling the resultant solution and isolating the hydrobromide salt of 1-[3-(dimethylamino)propyl]-1-(4-fluorophenyl)-1,3-dihydro-5-isobenzofuran carbonitrile.

We have found that the solvent system of dimethyl formamide and isopropanol is particularly useful for purification of hydrobromide salt of 1-[3-(dimethylamino)propyl]-1-(4-fluorophenyl)-1,3-dihydro-5-isobenzofuran carbonitrile.

In a preferred embodiment the hydrobromide salt of 1-[3-(dimethylamino)propyl]-1-(4-fluorophenyl)-1,3-dihydro-5-isobenzofuran carbonitrile is purified by recrystalization using solvent system of dimethyl formamide:isopropanol (DMF:IPA). The ratio of DMF:IPA may be between the range of 0.5:99.5 to 5:95 v/v, the preferred ratio being 2.5:97.5 v/v.

A process for recrystallization of the hydrobromide salt of [1-(3-dimethylamino)propyl)]-1-(4-fluorophenyl)-1,3-dihydro-5-halo-isobenzofuran comprises dissolving in a solvent system of dimethyl formamide:isopropanol between the range of 0.5:99.5 to 5:95 v/v at a temperature between the range of 30° C. to 90° C., cooling to a temperature between the range of 0° C. to 50° C. and maintaining the temperature for a period of about 0 to about 3 hours, isolating the hydrobromide salt of 1-[3-(dimethylamino)propyl]-1-(4-fluorophenyl)-1,3-dihydro-5-isobenzofuran carbonitrile.

In a preferred embodiment the hydrobromide salt of 1-[3-(dimethylamino)propyl]-1-(4-fluorophenyl)-1,3-dihydro-5-isobenzofuran carbonitrile may be dissolved in solvent system of dimethyl formamide and isopropanol by heating at about 80 to about 85° C., optionally charcolizing, cooling to about 25 to about 30° C. and maintaining the temperature at about 25 to about 30° C. for a period of about 2 to about 3 hours, filtering and isolating.

The recrystallization of hydrobromide salt of 1-[3-(dimethylamino)propyl]-1-(4-fluorophenyl)-1,3-dihydro-5-isobenzofuran carbonitrile using solvent system of dimethyl formamide and isopropanol provides the hydrobromide salt having a aspect ratio of less than about 2.

The recrystallization of hydrobromide salt of 1-[3-(dimethylamino)propyl]-1-(4-fluorophenyl)-1,3-dihydro-5-isobenzofuran carbonitrile using solvent system of dimethyl formamide and isopropanol provides the hydrobromide salt having a aspect ratio of less than about 2 and a bulk density of less than about 0.3 gm/ml and a tapped density of less than about 0.5 gm/ml.

The recrystallization of hydrobromide salt of 1-[3-(dimethylamino)propyl]-1-(4-fluorophenyl)-1,3-dihydro-5-isobenzofuran carbonitrile using solvent system of dimethyl formamide and isopropanol provides the hydrobromide salt having a aspect ratio of less than about 2 and particle size distribution as given below:

about 5% of particles having a particle size of less than 5 μm, about 25% of particles having a particle size of less than 15 μm, about 50% of particles having a particle size of less than 25 μm, about 75% of particles having a particle size of less than 40 μm, about 95% of particles having a particle size of less than 75 μm, about 100% of particles having a particle size of less than 200 μm.

The following examples are given by way of illustration only and not to be construed as limiting.

EXAMPLES

Example 1

5 gm crude citalopram base containing 4.84% of compound of formula 1, wherein X is Br (referred as bromo impurity) is taken in 50 ml ethyl acetate, 0.1 gm Pd/C is added and 0.1 gm sodium hypophosphite is added and heated to reflux, reflux maintained for 2 hrs.

Additional 0.1 gm sodium hypophosphite is taken in 1.0 ml water and added to the reaction mixture and reflux maintained for 2 hrs and presence of bromo impurity checked. Analysis showed that bromo impurity is absent.

Example 2

5 gm crude citalopram base containing 4.84% of compound of formula 1, wherein X is Br (referred as bromo impurity) is taken in 50 ml ethyl acetate, 0.1 gm Pd/C is added and 0.3 gm ammonium formate is added and heated to reflux, reflux maintained for 4 hrs, and presence of bromo impurity checked. Analysis showed that bromo impurity is absent.

Example 3

To the crude citalopram base oil (90 gm) having purity of 92.14 and containing 0.59% of impurity of compound of formula 1, (wherein X is bromo) and 1.95% of descyano impurity (a compound of formula 3) in 900 ml ethylacetate, 5 gm ammonium formate and 5 gm 50% wet Pd/C (5%) is added and heated to reflux (80–82° C.) and reflux maintained for 7 hrs, catalyst filtered, ethylacetate layer is washed with water and distilled. Analysis showed that the impurity of compound of formula 1 is absent and the descyano impurity has increased to 2.62% and citalopram purity has increased to 95.4%.

The above citalopram base oil is taken in 300 ml acetone and 42 gm oxalic acid is taken in 300 ml acetone and is added to the solution containing citalopram base and the precipitated oxalate salt is filtered and washed with chilled acetone and dried. Analysis showed that the descyano impurity has decreased to 1.18% and citalopram purity has increased to 98.26%.

The above oxalate salt is taken in toluene and water, basified with aqueous ammonia, toluene layer separated and washed with water, distilled to get a citalopram base oil which is taken in 600 ml IPA, 55 ml HBr in acetic acid is added stirred for 2 hours, the solvent is distilled out completely to get crude citalopram hydrobromide salt as a solid.

The crude citalopram hydrobromide salt is dissolved in 2 lit acetone at 45–50° C. and concentrated the acetone solution to 500 ml volume, cooled to 0–5° C., maintained at 0–5° C. for 1 hour and the product is filtered, washed with chilled acetone and dried. Analysis showed that the descyano impurity has decreased to 0.67% and citalopram purity has increased to 98.90%.

The above citalopram hydrobromide salt is dissolved in 200 ml methanol, charcolised with activated charcoal, filtered and washed with 50 ml methanol, concentrated the filtrate to 85 ml volume, 250 ml ethylacetate is added to the methanol solution containing the product at 25–30° C., maintained at 25–30° C. for 30 minutes, filtered the material and washed with ethyl acetate and dried. Analysis showed that the descyano impurity has decreased to 0.35% and citalopram purity has increased to 99.5%.

Example 4

Recrystallization of Citalopram Hydrobromide Salt Using Solvent System of Dimethylformamide and Isopropanol Citalopram hydrobromide is added to a mixture of dimethylformamide:isopropanol (DMF:IPA, ~2.5:97.5 v/v) to provide the concentration of 0.07 g/ml of IPA and 2.8 g/ml of DMF and heated to 80–85° C. and maintained for 1 hour for complete dissolution and charcolised the reaction mass at 80–85° C. and washed the charcoal bed with IPA (0.2 volume used with respect to IPA used for dissolution). Reaction mass is cooled to 20–25° C. in 2 hours period, stirred at 20–25° C. for 3 hours. The product is filtered and washed with IPA (0.1 volume used with respect to IPA used for dissolution) and dried in fluid bed drier at 45–60° C. for 10 hrs. % yield: 85%, Purity: 99.7%.

Aspect Ratio:

Instrument—Suitable optical microscope with Magnifications: 400×

Sample preparation—Take about 1–2 mg of API and add to 1–2 drops of paraffin oil, and make a smooth suspension.

Slide preparation—Prepare a thin uniform smear of the sample suspension on the clean dry glass slide and cover the smear with a cover slip.

Measurement of dimension—Take the prepared slide put on the platform of microscope. Focus a field with 400×oil immersion lens, freeze the image having discreet particles. Measure the length and breadth of each particle in the field. Length being defined as longest distance on one axis and Breadth being shortest distance on other axis.

Calculate the aspect ratio of each particle using the following formula $$\text{Aspect Ratio} = \frac{\text{Length}}{\text{Breadth}}$$

Calculate average Aspect ratio for at least 50 particles.

Particle Size:

Sample preparation—Transfer about 20 mg sample in 100 mL beaker, add 15 ml of diisopropyl ether and sonicate for 60 sec. to get a uniform slurry.

Instrumental Conditions—
INSTRUMENT: Malvern Mastersizer—S (or equivalent)
ANALYSIS MODEL: Polydisperse
PRESENTATION: 3NJE
RANGE LENS: 300 mm
BEAM LENGTH: 2.40 mm
RPM: 2000

Perform the background measurement using 100 ml of diisopropyl ether in liquid sampling device. When the blank correction is over, transfer about 2 to 5 ml aliquot of sample preparation into the device to get an obscuration value between 10% to 30%. When the obscuration value is stable, record the particle size histogram.

Density:

a) Bulk Density [Ref.: USP '26 <616> Method I]

Pass about 100 g of test sample through a 1.00 mm (No. 18) screen to break up agglomerates. Transfer about 250 ml test sample without compacting to a previously weighed and dried 250 ml cylinder (readable to 2 ml). Weigh accurately transferred test sample (W1). Read untapped volume of transferred test sample carefully (V1). Calculate bulk density as W1/V1 (g/ml).

(If it is not possible, to use 100 g of material, the test may be performed using suitable quantity of material with the 100 ml cylinder for apparent volume between 50 ml and 100 ml).

b) Tapped Density [Ref: USP '26 <616> Method II]

Mechanically tap the same cylinder prepared for bulk density test at the rate of 250 drops per minute using suitable tapped density tester that provides a fixed drop of 3 mm (±10%). Tap the cylinder 500 times initially and measure the tapped volume as V2. Repeat the tapping an additional 750 times and measure the tapped volume V3. If the difference between V2 and V3 is less than 2% then V3 is the final volume Vf, otherwise continue the tapping for 1250 times until the difference between succeeding measurements is less than 2%. Calculate tapped density as W1/Vf (g/ml).

Given below are the results of the analysis for particles of hydrobromide salt of [1-(3-dimethylamino)propyl)]-1-(4-fluorophenyl)-1,3-dihydro-5-halo-isobenzofuran (DMF:IPA recrystallization):

1] Particle Size Distribution—

5.6% particles are having a size less than 2.60 μm
24.02% particles are having a size less than 7.501 μm
52.29% particles are having a size less than 15.00 μm
76.57% particles are having a size less than 25.00 μm
100.0% particles are having a size less than 87.00 μm
Aspect ratio—1.81
Bulk density—0.261 gm/ml
Tapped density—0.453 gm/ml 2] Particle Size Distribution—

5.35% particles are having a size less than 2.60 μm
25.69% particles are having a size less than 7.50 μm
54.93% particles are having a size less than 15.00 μm
77.73% particles are having a size less than 25.00 μm
99.79% particles are having a size less than 87.00 μm
Aspect ratio—1.71
Bulk density—0.236 gm/ml
Tapped density—0.369 gm/ml 3] Particle Size Distribution—

6.15% particles are having a size less than 3.10 μm
27.39% particles are having a size less than 10.50 μm
53.93% particles are having a size less than 21.00 μm
78.02% particles are having a size less than 36.00 μm
99.83% particles are having a size less than 123.00 μm
Aspect ratio—1.88
Bulk density—0.277 gm/ml
Tapped density—0.412 gm/ml 4] Particle Size Distribution—

6.02% particles are having a size less than 1.30 μm
25.05% particles are having a size less than 3.70 μm
52.82% particles are having a size less than 9.00 μm
76.84% particles are having a size less than 18.00 μm
100.00% particles are having a size less than 51.00 μm
Aspect ratio—1.36

Example 5

Citalopram hydrobromide (40 g, purity 99.6%) is added to a mixture of dimethylformamide:isopropanol (DMF:IPA, 18 ml:600 ml) and heated at 85° C. for 1 hour for complete dissolution. It is cooled to 20–25° C. (room temp) in 2 hours and stirred at 20–25° C. for 3 hours. The product is filtered and washed with 100 ml IPA and dried in oven at 50–55° C. for 10–12 hrs. Dry wt=32.0 gm (Purity=99.8%).

This invention claimed is:

1. A process for decreasing the content of [1-(3-dimethylamino)propyl)]-1-(4-fluorophenyl)-1,3-dihydro-5-halo-isobenzofuran, a compound of formula 1, Formula 1

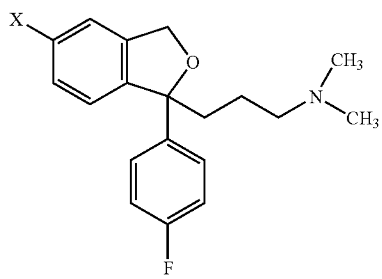

wherein X is halogen, by converting to a compound of formula 3, comprising

Formula 3

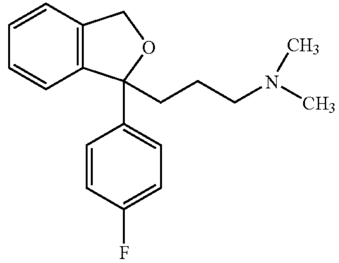

subjecting [1-(3-dimethylamino)propyl)]-1-(4-fluorophenyl)-1,3-dihydro-5-halo-isobenzofuran present as impurity in crude 1-[3-(dimethylamino)propyl]-1-(4-fluorophenyl)-1,3-dihydro-5-isobenzofuran carbonitrile to hydrogenolysis.

2. The process as claimed in claim 1, wherein the hydrogenolysis is carried out in presence of a catalyst and a hydrogen source.

3. The process as claimed in claim 2, wherein the catalyst is selected from palladium on carbon, platinum on carbon, rhodium on carbon and raney nickel.

4. The process as claimed in claim 3, wherein the catalyst is palladium on carbon.

5. The process as claimed in claim 2, wherein the hydrogen source is selected from ammonium formate, sodium hypophosphite and hydrogen.

6. The process as claimed in claim 5, wherein the hydrogen source is ammonium formate.

7. The process as claimed in claim 5, wherein the hydrogen source is sodium hypophosphite.

8. The process as claimed in claim 2, wherein the hydrogenolysis is carried out in an aqueous or non-aqueous solvent.

9. The process as claimed in claim 8, wherein the solvent is selected from ethyl acetate, dichloromethane, an alcohol, water or mixture thereof.

10. The process as claimed in claim 9, wherein the solvent is ethyl acetate.

11. The process as claimed in claim 8, wherein the hydrogenolysis is carried out at temperature between the range of 0° C. to 150° C.

12. The process as claimed in claim 11, wherein the hydrogenolysis is carried out at temperature between the range of 15° C. to 100° C.

13. The process as claimed in claim 12, wherein the hydrogenolysis is carried out at temperature between the range of 25° C. to 80° C.

14. The process as claimed in claim 8, wherein the hydrogenolysis is carried out for a period of about 30 minutes to about 24 hours.

15. The process as claimed in claim 14, wherein the hydrogenolysis is carried out for a period of about 1 to about 15 hours.

16. The process as claimed in claim 15, wherein the hydrogenolysis is carried out for a period of about 2 to about 7 hours.

17. The process as claimed in claim 2, wherein the catalyst is palladium on carbon and the hydrogen source is ammonium formate and the hydrogenolysis is carried out in ethyl acetate solvent at reflux temperature for a period of about 2 to about 7 hours.

18. The process as claimed in claim 2, wherein, the catalyst is palladium on carbon and the hydrogen source is sodium hypophosphite and the hydrogenolysis is carried out in ethyl acetate solvent at reflux temperature for a period of about 2 to about 7 hours.

19. The process as claimed in claim 2, wherein the catalyst is palladium on carbon and the hydrogen source is hydrogen and the hydrogenolysis is carried out at hydrogen pressure between the range of 0 to 100 psi.

20. The process as claimed in claim 2, wherein the catalyst is palladium on carbon and the hydrogen source is hydrogen and the hydrogenolysis is carried out at atmospheric pressure.

21. A process for purification of 1-[3-(dimethylamino) propyl]-1-(4-fluorophenyl)-1,3-dihydro-5-isobenzofuran carbonitrile comprising, a) subjecting crude 1-[3-(dimethylamino)propyl]-1-(4-fluorophenyl)-1,3-dihydro-5-isobenzofuran carbonitrile having impurity of [1-(3-dimethylamino)propyl)]-1-(4-fluorophenyl)-1,3-dihydro-5-halo-isobenzofuran, a compound of formula 1, Formula 1

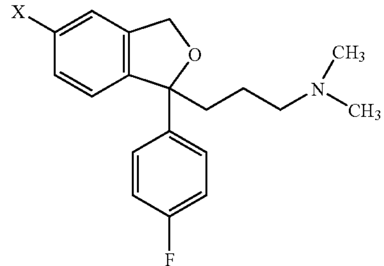

wherein X is halogen, to hydrogenolysis, b) optionally converting the resulting crude 1-[3-(dimethylamino)propyl]-1-(4-fluorophenyl)-1,3-dihydro-5-isobenzofuran carbonitrile to an acid addition salt thereof, and c) purifying and isolating the resulting 1-[3-(dimethylamino)propyl]-1-(4-fluorophenyl)-1,3-dihydro-5-isobenzofuran carbonitrile as a base or a pharmaceutically acceptable salt thereof.

22. The process as claimed in claim 21, wherein the pharmaceutically acceptable salt of 1-[3-(dimethylamino) propyl]-1-(4-fluorophenyl)-1,3-dihydro-5-isobenzofuran carbonitrile is obtained having purity greater than 99.5%.

23. The process as claimed in claim 22, wherein pharmaceutically acceptable salt of 1-[3-(dimethylamino)propyl]-1-(4-fluorophenyl)-1,3-dihydro-5-isobenzofuran carbonitrile is obtained having purity greater than 99.8%.

* * * * *